United States Patent
Haque (10) Patent No.: US 6,339,085 B1
(45) Date of Patent: Jan. 15, 2002

(54) THERAPEUTICS FOR CARDIOVASCULAR AND RELATED DISEASES

(75) Inventor: Wasimul Haque, Edmonton, Alberta (CA)

(73) Assignees: The University of Manitoba; Medicore Inc., both of Winnepeg (CA)

(*) Notice: Subject to any disclaimer, the term of this patent is extended or adjusted under 35 U.S.C. 154(b) by 0 days.

(21) Appl. No.: 09/520,194

(22) Filed: Mar. 7, 2000

Related U.S. Application Data (60) Provisional application No. 60/125,881, filed on Mar. 24, 1999, and provisional application No. 60/123,698, filed on Mar. 8, 1999.

(51) Int. Cl.[7] ............... A61K 31/4375; A61K 31/5377; C07D 413/14; C07D 471/02
(52) U.S. Cl. .................... 514/233.8; 514/302; 544/127; 546/116
(58) Field of Search ........................... 514/302; 546/116

(56) References Cited

U.S. PATENT DOCUMENTS

| | | |
|---|---|---|
| 3,206,463 A | 9/1965 | Baetz |
| 3,910,921 A | 10/1975 | Esanu |
| 3,987,177 A | 10/1976 | Giudicelli et al. |
| 4,032,534 A | 6/1977 | Chodkiewicz |
| 4,036,844 A | 7/1977 | Thorne et al. |
| 4,053,607 A | 10/1977 | Thorne et al. |
| 4,137,316 A | 1/1979 | Esanu |
| 4,167,562 A | 9/1979 | Evers |
| 4,361,570 A | 11/1982 | Fici |
| 4,369,172 A | 1/1983 | Schor et al. |

(List continued on next page.)

FOREIGN PATENT DOCUMENTS

| | | |
|---|---|---|
| BE | 831350 | 1/1976 |
| BE | 863754 | 5/1978 |
| CH | 561 183 | 4/1975 |
| DE | 1 958 226 | 5/1970 |
| DE | 24 61 742 | 7/1976 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 846376 | 3/1941 |
| FR | 1323941 | 12/1963 |
| FR | 5552 | 12/1967 |
| FR | 6453 | 12/1968 |
| FR | 1579544 | 8/1969 |
| FR | 2101010 | 3/1972 |
| FR | 2255883 | 7/1975 |
| FR | 2428640 | 1/1980 |
| GB | 1 013 939 | 12/1965 |
| GB | 1 201 014 | 8/1970 |
| GB | 1 297 080 | 11/1972 |
| GB | 1 360 536 | 7/1974 |
| GB | 1 493 993 | 12/1977 |
| GB | 2 254 556 | 10/1992 |
| JP | 48-21959 | 7/1973 |
| JP | 54-17130 | 2/1979 |
| WO | WO 83/00085 | 1/1983 |
| WO | WO 91/19500 | 12/1991 |
| WO | WO 94/18965 | 9/1994 |
| WO | WO 99/03365 | 1/1999 |

OTHER PUBLICATIONS

"B Vitamins May Cut Heart Disease Risk", *Harvard Health Letter*, 1 page (1998).

Barrett, S., "Homocysteine: A Cardiovascular Risk Factor Worth Considering", http://www.quackwatch.com/03HealthPromotion/homocysteine.html, 2 pages (©1997).

Bernstein, A., "Vitamin $B_6$ in Clinical Neurology", *Annals of New York Academy of Sciences*, vol. 585, pp. 250–260 (1990).

Berger, A. R. et al., "Dose response, coasting, and differential fiber vulnerability in human toxic neuropathy: A prospective study of pyridoxine neurotoxicity", *Neurology*, vol. 42, No. 7, pp. 1367–1370 (Jul. 1992).

Bode, W. et al., "Pyridoxal–5'–Phosphate and Pyridoxal Biokinetics in Male Wistar Rats Fed Graded Levels of Vitamin B–6", *J. Nutr.*, vol. 121, No. 11, pp. 1738–1745 (Nov. 1991).

Chasan–Taber, L. et al., "A Prospective Study of Folate and Vitamin $B_6$ and Risk of Myocardial Infarction in US Physicians", *Journal of the American College of Nutrition*, vol. 15, No. 2, pp. 136–143 (Apr. 1996).

(List continued on next page.)

*Primary Examiner*—Deborah C. Lambkin
*Assistant Examiner*—Sonya N. Wright
(74) *Attorney, Agent, or Firm*—Merchant & Gould P. C.

(57) ABSTRACT

Pyridoxal analogues can be useful for treating $B_6$ efficiency and related diseases; cardiovascular and related diseases; melanoma and related diseases; and symptoms thereof. One such analogue is a compound of the formula:

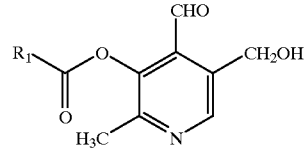

or a pharmaceutically acceptable acid addition salt thereof, in which $R_1$ is alkyl, alkenyl, in which alkyl or alkenyl can be interrupted by nitrogen, oxygen, or sulfur, and can be substituted at the terminal carbon by hydroxy, alkoxy, alkanoyloxy, alkanoyloxyaryl, alkoxyalkanoyl, alkoxycarbonyl, or dialkylcarbamoyloxy; alkoxy; dialkylamino; alkanoyloxy; alkanoyloxyaryl; alkoxyalkanoyl; alkoxycarbonyl; dialkylcarbamoyloxy; or aryl, aryloxy, arylthio, or aralkyl, in which aryl can be substituted by alkyl, alkoxy, amino, hydroxy, halo, nito, or alkanoyloxy. These analogues can be administered, either alone or concurrently with known medications, to treat the above-described diseases.

57 Claims, 4 Drawing Sheets

U.S. PATENT DOCUMENTS

| | | | |
|---|---|---|---|
| 4,374,841 | A | 2/1983 | Descamps et al. |
| 4,515,771 | A | 5/1985 | Fine |
| 4,567,179 | A | 1/1986 | Lombardino |
| 4,569,938 | A * | 2/1986 | Esanu ........................ 514/302 |
| 4,569,939 | A * | 2/1986 | Esanu ........................ 514/302 |
| 4,581,363 | A | 4/1986 | Esanu |
| 4,605,741 | A | 8/1986 | Zagnoli et al. |
| 4,730,042 | A | 3/1988 | Hege et al. |
| 4,735,950 | A | 4/1988 | Esanu |
| 4,735,956 | A | 4/1988 | Baldwin et al. |
| 4,837,239 | A | 6/1989 | Benjamin et al. |
| 4,843,071 | A | 6/1989 | Hohenwarter |
| 4,962,121 | A | 10/1990 | Hamberger et al. |
| 5,001,115 | A | 3/1991 | Sloan |
| 5,053,396 | A | 10/1991 | Blass |
| 5,118,505 | A | 6/1992 | Költringer |
| 5,130,324 | A | 7/1992 | Ulrich et al. |
| 5,132,115 | A | 7/1992 | Wolter et al. |
| 5,210,083 | A | 5/1993 | Pfirrmann |
| 5,213,813 | A | 5/1993 | Kornecki et al. |
| 5,254,557 | A * | 10/1993 | Buckle et al. .............. 514/269 |
| 5,254,572 | A | 10/1993 | Serfontein |
| 5,272,165 | A | 12/1993 | Ulrich et al. |
| 5,278,154 | A | 1/1994 | Lacoste et al. |
| 5,288,716 | A | 2/1994 | Speck |
| 5,326,757 | A | 7/1994 | Demopoulos |
| 5,328,453 | A | 7/1994 | Sibalis |
| 5,372,999 | A | 12/1994 | Schneider et al. |
| 5,385,937 | A | 1/1995 | Stamler et al. |
| 5,420,112 | A | 5/1995 | Lewis et al. |
| 5,441,972 | A | 8/1995 | Ogata et al. |
| 5,504,090 | A | 4/1996 | Neely |
| 5,563,126 | A | 10/1996 | Allen et al. |
| 5,569,459 | A | 10/1996 | Shlyankevich |
| 5,569,648 | A | 10/1996 | Lewis et al. |
| 5,631,271 | A | 5/1997 | Serfontein |
| 5,633,228 | A | 5/1997 | Lewis et al. |
| 5,648,335 | A | 7/1997 | Lewis et al. |
| 5,728,684 | A | 3/1998 | Cheng et al. |
| 5,733,884 | A | 3/1998 | Barbul et al. |
| 5,733,916 | A | 3/1998 | Neely |
| 5,770,215 | A | 6/1998 | Moshyedi |
| 5,795,873 | A | 8/1998 | Allen |
| 5,804,163 | A | 9/1998 | Gibby et al. |
| 5,804,594 | A | 9/1998 | Murad |
| 5,833,998 | A | 11/1998 | Biedermann et al. |
| 5,834,446 | A | 11/1998 | Dow et al. |
| 5,840,685 | A | 11/1998 | Fujii et al. |
| 5,847,008 | A | 12/1998 | Doebber et al. |
| 5,858,017 | A | 1/1999 | Demopolus et al. |
| 5,859,051 | A | 1/1999 | Adams et al. |
| 5,874,420 | A | 2/1999 | Pelleg |
| 5,874,443 | A | 2/1999 | Kiely et al. |
| 5,888,514 | A | 3/1999 | Weisman |

OTHER PUBLICATIONS

Cho, Y. et al., "In Vivo Evidence for a Vitamin B–6 Requirement in Carnitine Synthesis", *J. Nutr.*, vol. 120, pp. 258–265 (1990).

"Computer Generated Search Reports", 70 pages (May 1999).

Ellis, J. et al., "Prevention of Myocardial Infarction by Vitamin $B_6$", *Res. Commun. Molec. Pathol. Pharmacol.*, vol. 89, No. 2, pp. 208–220 (Aug. 1995).

Harada, K. et al., "Studies on Vitamin $B_6$.(IV) Behavior of Pyridoxal Acylates in the Body After Parenteral Administration", *Vitamins Journal of the Vitamin Society of Japan*, vol. 45, No. 2, pp. 69–75 (Feb. 1972).

Hoover, D.M. et al., "Ultrastructural Lesions of Pyridoxine Toxicity in Beagle Dogs", *Vet. Pathol.*, vol. 18, pp. 769–777 (1981).

Kok, F. et al., "Low Vitamin $B_6$ Status in Patients with Acute Myocardial Infarction", *Am. J. Cardiol.*, vol. 63, pp. 513–516 (Mar. 1, 1989).

Krinke, G. et al., "Pyridoxine Megavitaminosis: An Analysis of the Early Changes Induced with Massive Doses of Vitamin $B_6$ in Rat Primary Sensory Neurons", *J. Neuopathol Exp. Neurol.*, vol. 44, No. 7, pp. 117–129 (Mar. 1985).

Lal, K. et al., "Hypotensive action of 5–HT receptor agonists in the vitamin $B_6$–deficient hypertensive rat", *Eur. J. Pharmacol.*, vol. 234 Nos. 2/3, pp. 183–189 (Apr. 1993).

Lal, K. et al., "Calcium channels in vitamin $B_6$ deficiency––induced hypertension", *Journal of Hypertension*, vol. 11, No. 12, pp. 1357–1362 (Dec. 1993).

Lal, K. et al., "The effect of vitamin $B_6$ on the systolic blood pressure of rats in various animals models of hypertension", *Journal of Hypertension*, vol. 14, No. 3, pp. 355–363 (Mar. 1996).

Merrill, Jr. et al. A. et al., "Diseases associated with defects in vitamin $B_6$ metabolism or utilization", *Ann. Rev. Nutr.*, vol. 7, pp. 137–156 (1987).

Omenn, G. et al., "Preventing Coronary Heart Disease", *Circulation*, vol. 97, pp. 421–424 (1998).

Paulose, C. et al., "Sympathetic Stimulation and Hypertension in the Pyridoxine–Deficient Adult Rat", *Hypertension*, vol. 11, No. 4, pp. 387–391 (Apr. 1988).

Rimm, E. et al., "Folate and Vitamin $B_6$ From Diet and Supplements in Relation to Risk of Coronary Heart Disease Among Women", *JAMA*, vol. 279, No. 5, pp. 359–364 (Feb. 4, 1998).

Trezise, D. et al., "$P_2$ purinoceptor anatagonist properties of pyridoxal–5–phosphate", *Eur. J. Pharmacol.*, vol. 259, No. 3, pp. 295–300 (Jul. 11, 1994).

Verhoef, P. et al. "Homocysteine Metabolism and Risk of Myocardial Infarction: Relation with Vitamins$_6$, $B_{12}$, and Folate", *Am. J. Epidemiol.*, vol. 143, No. 9, pp. 845–859 (May 1, 1996).

Vermaak, W.J.H. et al., "Vitamin $B_6$ and coronary artery disease. Epidemiological observations and case studies", *Atherosclerosis*, vol. 63, pp. 235–238 (Feb. 1987).

Windebank, A., "Neurotoxicity of Pyridoxine Analogs Is Related to Coenzyme Structure", *Neurochemical Pathology*, vol. 3, pp. 159–167 (1985).

Zempleni, J. et al., "The utilization of intravenously infused pyridoxine in humans", *Clinica Chimica Acta*, vol. 229, Nos. 1, 2, pp. 27–36 (Sep. 1994).

Sakuragi, T. et al., "The Synthesis of Long Chain Fatty Acid Derivatives of the Vitamin $B_6$ Group", *J. Am. Chem. Soc.*Vol. 78, pp. 839–842 (Feb. 20, 1956).

Tanaka, T. et al., "Pyridoxine Derivatives", *Chemical Abstracts*, vol. 62, No. 12, 1 page (Jun. 7, 1965).

Viscontini, V. et al., "Über einige Derivate des Pyridoxals", *Helvetica Chimica Acta*, vol. 34, No. 296, pp. 2438–2439 (1951).

Korytnyk et al. Schiff Bases of Pyridoxal: Their Structure and the Stabilization of their Ring–Chain Tautomeric Forms by Acylation, Tetrahedron, 26 (23), 5415–25, 1970.*

* cited by examiner-

THERAPEUTICS FOR CARDIOVASCULAR AND RELATED DISEASES

This application claims the benefit of U.S. Provisional Application No. 60/125,881 filed Mar. 24, 1999 which claims the benefit of U.S. Provisional Application No. 60/123,698 filed Mar. 8, 1999.

FIELD OF THE INVENTION

This invention relates to 3-acylated pyridoxal analogues and pharmaceutical compositions thereof and to treatments for cardiovascular and related diseases, for example, hypertrophy, hypertension, congestive heart failure, myocardial ischemia, arrhythmia, heart failure subsequent to myocardial infarction, myocardial infarction, ischemia reperfusion injury, blood coagulation, platelet aggregation, and diseases that arise from thrombotic and prothrombotic states in which the coagulation cascade is activated; treatments for vitamin $B_6$ deficiency and related diseases, for example, hyperhomocysteinemia; and treatments for melanoma and related diseases.

BACKGROUND

Pyridoxal-5'-phosphate (PLP), an end product of vitamin $B_6$ metabolism, plays a vital role in mammalian health. Vitamin $B_6$ typically refers to pyridoxine, which is chemically known as 2-methyl-3-hydroxy-4,5-di(hydroxymethyl)pyridine and is represented by formula I:

I

Yet two additional compounds, pyridoxal of formula II

II and pyridoxamine of formula III

III are also referred to as vitamin $B_6$. All three compounds serve as precursors to pyridoxal-5'-phosphate (PLP), which is chemically known as 3-hydroxy-2-methyl-5-[(phosphonooxy) methyl]-4-pyridine-carboxaldehyde and is represented by formula IV:

IV

PLP is the biologically active form of vitamin $B_6$ inside cells and in blood plasma. Mammals cannot synthesize PLP de novo and must rely on dietary sources of the precursors pyridoxine, pyridoxal, and pyridoxamine, which are metabolized to PLP. For instance, mammals produce PLP by phosphorylating pyridoxine by action of pyridoxal kinase and then oxidizing the phosphorylated product. PLP can also be chemically synthesized by, for example, reacting ATP with pyridoxal, reacting phosphorus oxychloride with pyridoxal in aqueous solution, and reacting pyridoxamine with concentrated phosphoric acid and then oxidizing the phosphorylated product.

PLP is a regulator of biological processes and a cofactor in more than 100 enzymatic reactions. It has been shown to be an antagonist of a purinergic receptor, thereby affecting ATP binding; it has been implicated in modulation of platelet aggregation; it is an inhibitor of certain phosphatase enzymes; and it has been implicated in the control of gene transcription. PLP is also a coenzyme in certain enzyme-catalyzed processes, for example, in glycogenolysis at the glycogen phosphorylase level, in the malate asparatate shuttle involving glycolysis and glycogenolysis at the transamination level, and in homocysteine metabolism.

Mammals may have deficiencies in PLP synthesis or function because of inadequate dietary uptake of precursors or antagonism of PLP synthesis or PLP function as a coenzyme as a result of, for example, genetic defects or a drug binding to PLP to make an intermediate that inhibits an enzyme in the PLP metabolic pathway or a drug inhibiting another step in the synthesis of PLP. There are situations where high, sustained plasma levels of PLP can provide a desirable therapeutic effect, particularly with respect to cardiovascular health.

To boost mammalian PLP levels, lipophilic PLP precursors that are metabolized in vivo to PLP have been administered. Although the administration of some compounds have shown some therapeutic benefits, there have been disadvantages associated with the compounds disclosed to date, such as, for example, excretion, rapid or inefficient metabolism, and toxicity.

Thus, there is a need to identify and administer drugs that are readily absorbed and converted to PLP in the blood or inside cells; that more slowly metabolize to PLP in vivo to ultimately maintain sustained levels of PLP, to lessen loss by excretion, and to decrease the likelihood of neurotoxicity; or that beneficially affect PLP-related conditions.

SUMMARY OF THE INVENTION

The present invention provides for 3-acylated pyridoxal analogues. One embodiment of the invention includes a 3-acylated analogue of pyridoxal (2-methyl-3-hydroxy-4- formyl-5-hydroxymethylpyridine), which is a compound of formula V:

V or a pharmaceutically acceptable acid addition salt thereof; wherein
$R_1$ is alkyl,
  alkenyl,
    in which alkyl or alkenyl can be interrupted by nitrogen, oxygen, or sulfur, and can be substituted at the terminal carbon by hydroxy, alkoxy, alkanoyloxy, alkanoyloxyaryl, alkoxyalkanoyl, alkoxycarbonyl, or dialkylcarbamoyloxy;
  alkoxy;
  dialkylamino;
  alkanoyloxy;
  alkanoyloxyaryl;
  alkoxyalkanoyl;
  alkoxycarbonyl;
  dialkylcarbamoyloxy; or
  aryl,
  aryloxy,
  arylthio, or
  aralkyl,
    in which aryl can be substituted by alkyl, alkoxy, amino, hydroxy, halo, nitro, or alkanoyloxy.

Another embodiment of the invention is a 3-acylated analogue of pyridoxal-4,5-aminal (1-secondary amino-1,3-dihydro-7-hydroxy-6-methylfuro(3,4-c)pyridine), which is a compound of formula VI:

VI or a pharmaceutically acceptable acid addition salt thereof; wherein
$R_1$ is alkyl,
  alkenyl,
    in which alkyl or alkenyl can be interrupted by nitrogen, oxygen, or sulfur, and can be substituted at the terminal carbon by hydroxy, alkoxy, alkanoyloxy, alkanoyloxyaryl, alkoxyalkanoyl, alkoxycarbonyl, or dialkylcarbamoyloxy;
  alkoxy;
  dialkylamino;
  alkanoyloxy;
  alkanoyloxyaryl;
  alkoxyalkanoyl;
  alkoxycarbonyl;
  dialkylcarbamoyloxy; or
  aryl,
  aryloxy,
  arylthio, or
  aralkyl,
    in which aryl can be substituted by alkyl, alkoxy, amino, hydroxy, halo, nitro, or alkanoyloxy; and
$R_2$ is a secondary amino group.

In another aspect, the invention is directed to a pharmaceutical composition that includes a pharmaceutically acceptable carrier and a therapeutically effective amount of a compound of formula V or VI.

The invention is also directed to a method of treating vitamin $B_6$ deficiency and related diseases, for example, hyperhomocysteinemia, by administering a therapeutically effective amount of a compound of formula V or VI in a unit dosage form.

In another aspect, the invention is directed to a method of treating cardiovascular and related diseases, for example, hypertension, hypertrophy, arrhythmia, congestive heart failure, myocardial ischemia, heart failure subsequent to myocardial infarction, myocardial infarction, ischemia reperfusion injury, blood coagulation, platelet aggregation, and diseases that arise from thrombotic and prothrombotic states in which the coagulation cascade is activated by administering a therapeutically effective amount of a compound of formula V or VI in a unit dosage form. For such a method, a compound of formula V or VI can be administered alone or concurrently with a known therapeutic cardiovascular agent, for example, angiotensin converting enzyme inhibitor, an angiotensin II receptor antagonist, a vasodilator, a diuretic, an α-adrenergic receptor antagonist, an antioxidant, or a mixture thereof.

In still another aspect, the invention is directed to a method of treating melanoma and related diseases by administering a therapeutically effective amount of a compound of formula V or VI in a unit dosage form. For such a method, a compound of formula V or VI can be administered alone or concurrently with known medicaments suitable for treating melanoma and related diseases, for example, interleukin-2 immunotherapy.

DESCRIPTION OF THE INVENTION

The present invention provides for 3-acylated pyridoxal analogues, pharmaceutical compositions, and methods for treatment of cardiovascular and related diseases, vitamin $B_6$ deficiency and related diseases, and melanoma and related diseases.

Cardiovascular and related diseases include, for example, hypertension, hypertrophy, congestive heart failure, heart failure subsequent to myocardial infarction, arrhythmia, myocardial ischemia, myocardial infarction, ischemia reperfusion injury, blood coagulation, platelet aggregation, and diseases that arise from thrombotic and prothrombotic states in which the coagulation cascade is activated.

Heart failure is a pathophysiological condition in which the heart is unable to pump blood at a rate commensurate with the requirement of the metabolizing tissues or can do so only from an elevated filling pressure (increased load). Thus, the heart has a diminished ability to keep up with its workload. Over time, this condition leads to excess fluid accumulation, such as peripheral edema, and is referred to as congestive heart failure.

When an excessive pressure or volume load is imposed on a ventricle, myocardial hypertrophy (i.e., enlargement of the heart muscle) develops as a compensatory mechanism. Hypertrophy permits the ventricle to sustain an increased load because the heart muscle can contract with greater force. However, a ventricle subjected to an abnormally elevated load for a prolonged period eventually fails to sustain an increased load despite the presence of ventricular hypertrophy, and pump failure can ultimately occur.

Heart failure can arise from any disease that affects the heart and interferes with circulation. For example, a disease that increases the heart muscle's workload, such as hypertension, will eventually weaken the force of the heart's contraction. Hypertension is a condition in which there is an increase in resistance to blood flow through the vascular system. This resistance leads to increases in systolic and/or diastolic blood pressures. Hypertension places increased tension on the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Ischemia is a condition in which an organ or a part of the body fails to receive a sufficient blood supply. When an organ is deprived of a blood supply, it is said to be hypoxic. An organ will become hypoxic even when the blood supply temporarily ceases, such as during a surgical procedure or during temporary artery blockage. Ischemia initially leads to a decrease in or loss of contractile activity. When the organ affected is the heart, this condition is known as myocardial ischemia, and myocardial ischemia initially leads to abnormal electrical activity. This can generate an arrhythmia. When myocardial ischemia is of sufficient severity and duration, cell injury can progress to cell death—i.e., myocardial infarction—and subsequently to heart failure, hypertrophy, or congestive heart failure.

When blood flow resumes to an organ after temporary cessation, this is known as ischemic reperfusion of the organ. For example, reperfusion of an ischemic myocardium can counter the effects of coronary occlusion, a condition that leads to myocardial ischemia. Ischemic reperfusion to the myocardium can lead to reperfusion arrhythmia or reperfusion injury. The severity of reperfusion injury is affected by numerous factors, such as, for example, duration of ischemia, severity of ischemia, and speed of reperfusion. Conditions observed with ischemia reperfusion injury include neutrophil infiltration, necrosis, and apoptosis.

Drug therapies, using known active ingredients such as vasodilators, angiotensin II receptor antagonists, angiotensin converting enzyme inhibitors, diuretics, antithrombolytic agents, β-adrenergic receptor antagonists, α-adrenergic receptor antagonists, calcium channel blockers, and the like, are available for treating cardiovascular and related diseases.

Vitamin $B_6$ deficiency and related diseases include hyperhomocysteinemia and interferences in pathways in which PLP is a coenzyme, for example, glycolysis and aerobic metabolism as well as biosynthesis of neurotransmitters 5-hydroxytryptamine (serotonin) and γ-aminobutyric acid.

Melanoma and related diseases include cancer that originates in the pigment-producing cells of the skin and metastasized cancer that originated in the pigment-producing cells of the skin. Available treatments include surgery, chemotherapy, and interleukin-2 immunotherapy.

The invention is generally directed to 3-acylated pyridoxal analogues, compositions including these analogues, and methods of administering pharmaceutical compositions containing a therapeutically effective amount of at least one of these analogues to treat vitamin $B_6$ deficiency and related diseases, cardiovascular and related diseases, and melanoma and related diseases.

Although this invention is not limited to any particular theory, an analogue according to the invention can be advantageous for absorption and concentration because of the acylation. To enhance absorption from the digestive tract and across biological membranes, polar groups on a drug molecule can be blocked with lipophilic functions that will be enzymatically cleaved off from the drug after absorption into the circulatory system. Lipophilic moieties can also improve site-specificity and bioavailability of the drug. The speed at which the blocking groups are removed can be used to control the rate at which the drug is released. The blocking of polar groups on the drug can also slow first-pass metabolism and excretion. Phenolic hydroxy groups are particularly susceptible to glucoronidation and/or sulfonation, reactions that often precede excretion. To reduce metabolism and excretion of phenolic drugs, an ester can be used. An ester is a common blocking group that is readily hydrolyzed from the drug by endogenous esterases. Bundgaard, *Design and Application of Prodrugs in A Textbook of Drug Design and Development* Ch. 5 (Krogsgaard-Larson & Bundgaard, eds., Hardwood Academic Publishers, Reading, United Kingdom 1991).

The compounds of the invention are 3-acylated analogues of pyridoxal. One aspect of the invention is a 3-acylated analogue of pyridoxal (2-methyl-3-hydroxy-4-formyl-5-hydroxymethylpyridine), which is a compound of formula V:

or a pharmaceutically acceptable acid addition salt thereof;
wherein
$R_1$ is alkyl,
  alkenyl,
    in which alkyl or alkenyl can be interrupted by nitrogen, oxygen, or sulfur, and can be substituted at the terminal carbon by hydroxy, alkoxy, alkanoyloxy, alkanoyloxyaryl, alkoxyalkanoyl, alkoxycarbonyl, or dialkylcarbamoyloxy;
  alkoxy;
  dialkylamino;
  alkanoyloxy;
  alkanoyloxyaryl;
  alkoxyalkanoyl;
  alkoxycarbonyl;
  dialkylcarbamoyloxy; or
  aryl,
  aryloxy, arylthio, or
aralkyl,
    in which aryl can be substituted by alkyl, alkoxy, amino, hydroxy, halo, nitro, or alkanoyloxy.

The term "alkyl" includes a straight or branched saturated aliphatic hydrocarbon chain having from 1 to 8 carbon atoms, such as, for example, methyl, ethyl, propyl, isopropyl (1-methylethyl), butyl, tert-butyl (1,1-dimethylethyl), and the like.

The term "alkenyl" includes an unsaturated aliphatic hydrocarbon chain having from 2 to 8 carbon atoms, such as, for example, ethenyl, 1-propenyl, 2-propenyl, 1-butenyl, 2-methyl-1-propenyl, and the like.

The above alkyl or alkenyl can optionally be interrupted in the chain by a heteroatom, such as, for example, a nitrogen, sulfur, or oxygen atom, forming an alkylaminoalkyl, alkylthioalkyl, or alkoxyalkyl, for example, methylaminoethyl, ethylthiopropyl, methoxymethyl, and the like.

The above alkyl or alkenyl can optionally be substituted at the terminal carbon by hydroxy, alkoxy, alkanoyloxyaryl, alkanoyloxy, alkoxyalkanoyl, alkoxycarbonyl, or dialkylcarbamoyloxy.

The term "alkoxy" includes alkyl as defined above joined to an oxygen atom having preferably from 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

The term "dialkylamino" includes two alkyl groups as defined above joined to a nitrogen atom, in which alkyl has preferably 1 to 4 carbon atoms, such as, for example, dimethylamino, diethylamino, methylethylamino, methylpropylamino, diethylamino, and the like.

The term "alkanoyloxy" includes a group of the formula Examples of alkanoyloxy include methanoyloxy, ethanoyloxy, propanoyloxy, and the like. Examples of alkyl substituted at the terminal carbon by alkanoyloxy include 1-ethanoyloxy-1-methylethyl, propanoyloxy-1-methylethyl, and the like.

The term "alkanoyloxyaryl" includes a group of the formula

Examples of alkanoyloxyaryl include methanoyloxyphenyl, ethanoyloxyphenyl, propanoyloxyphenyl, and the like.

The term "aryl" includes aromatic hydrocarbyl, including fused aromatic rings, such as, for example, phenyl and naphthyl.

The term "aryloxy" includes aryl having an oxygen atom bonded to an aromatic ring, such as, for example, phenoxy and naphthoxy.

The term "arylthio" includes aryl having a sulfur atom bonded to an aromatic ring, such as, for example, phenylthio and naphthylthio.

The term "aralkyl" includes aryl having alkyl bonded to an aromatic ring, such as, for example, benzyl and naphthylmethyl.

Aryl from any of aryl, aryloxy, arylthio, aralkyl, and alkanoyloxyaryl can be unsubstituted or can be substituted on a ring by, for example, $C_{1-4}$ alkyl, $C_{1-4}$ alkoxy, amino, hydroxy, nitro, halo, or alkanoyloxy. Examples of substituted aryl include toluyl, methoxyphenyl, ethylphenyl, and the like.

The term "alkoxyalkanoyl" includes a group of the formula

Examples of alkoxyalkanoyl include (2-acetoxy-2-methyl) propanyl, 3-ethoxy-3-propanoyl, 3-methoxy-2-propanoyl, and the like.

The term "alkoxycarbonyl" includes a group of the formula

Examples of alkoxycarbonyl include methoxycarbonyl, ethoxycarbonyl, propoxycarbonyl, and the like.

The term "dialkylcarbamoyloxy" includes a group of the formula

Examples of dialkylcarbamoyloxy include dimethylaminomethanoyloxy, 1-ethyl-1-methylaminomethanoyloxy, and the like. Examples of alkyl substituted at the terminal carbon by alkanoyloxy include dimethylamino-1-methylethyl, 1-ethyl-1-methylaminomethanoyloxy-1-methlethyl, and the like.

The term "halo" includes bromo, chloro, and fluoro. Preferably halo is fluoro.

$R_1$ groups for compounds of formula V can be toluyl, naphthyl, phenyl, phenoxy, dimethylamino, 2,2-dimethylethyl, ethoxy, (2-acetoxy-2-methyl)propanyl, 1-ethanoyloxy-1-methylethyl, tert-butyl, acetylsalicyl, and ethanoyloxyphenyl.

Preferred $R_1$ groups for compounds of formula V are toluyl or naphthyl. Such $R_1$ groups when joined with a carbonyl group form an acyl group which preferred for compounds of formula V include toluoyl or β-naphthoyl. Of the toluoyl group, the p-isomer is more preferred.

Examples of 3-acylated analogues of pyridoxal include, but are not limited to, 2-methyl-3-toluoyloxy-4-formyl-5-hydroxymethylpyridine and 2-methyl-βnaphthoyloxy-4-formyl-5-hydroxymethylpyridine.

Another aspect of the invention is a 3-acylated analogue of pyridoxal-4,5-aminal (1-secondary amino-1,3-dihydro-7- hydroxy-6-methylfuro(3,4-c)pyridine), which is a compound of formula VI:

or a pharmaceutically acceptable acid addition salt thereof, wherein
  $R_1$ is alkyl,
    alkenyl,
      in which alkyl or alkenyl can be interrupted by nitrogen, oxygen, or sulfur, and can be substituted at the terminal carbon by hydroxy, alkoxy, alkanoyloxy, alkanoyloxyaryl, alkoxyalkanoyl, alkoxycarbonyl, or dialkylcarbamoyloxy;
    alkoxy;
    dialkylamino;
    alkanoyloxy;
    alkanoyloxyaryl;
    alkoxyalkanoyl;
    alkoxycarbonyl;
    dialkylcarbamoyloxy; or
    aryl,
    aryloxy,
    arylthio, or
    aralkyl,
      in which aryl can be substituted by alkyl, alkoxy, amino, hydroxy, halo, nitro, or alkanoyloxy; and
  $R_2$ is a secondary amino group.

The terms "alkyl," "alkenyl," "alkoxy," "dialkylamino," "alkanoyloxy," "alkanoyloxyaryl," "alkoxyalkanoyl," "alkoxycarbonyl," "dialkylcarbamoyloxy," "halo," "aryl," "aryloxy," "arylthio," and "aralkyl" are as defined above.

The term "secondary amino" group includes a group of formula VII:

derived from a secondary amine $R_3R_4NH$, in which $R_3$ and $R_4$ are each independently alkyl, alkenyl, cycloalkyl, aryl, or, when $R_3$ and $R_4$ are taken together, may form a ring with the nitrogen atom and which may be interrupted by a heteroatom, such as, for example, a nitrogen, sulfur, or oxygen atom. The terms "alkyl," "alkenyl," and "aryl" are used as defined above in forming secondary amino groups such as, for example, dimethylamino, methylethylamino, diethylamino, dialkylamino, phenylmethylamino, diphenylamino, and the like.

The term "cycloalkyl" refers to a saturated hydrocarbon having from 3 to 8 carbon atoms, preferably 3 to 6 carbon atoms, such as, for example, cyclopropyl, cyclopentyl, cyclohexyl, and the like.

When $R_3$ and $R_4$ are taken together to form a ring with the nitrogen atom, a cyclic secondary amino group, such as, for example, piperidino, can be formed. And, when the cyclic secondary amino group is interrupted with a heteroatom, a group such as, for example, piperazino or morpholino can be formed.

$R_1$ groups for compounds of formula VI can be toluyl, naphthyl, phenyl, phenoxy, dimethylamino, 2,2-dimethylethyl, ethoxy, (2-acetoxy-2-methyl)propanyl, 1-ethanoyloxy-1-methylethyl, tert-butyl, acetylsalicyl, and ethanoyloxyphenyl.

Preferred $R_1$ groups for compounds of formula VI include toluyl, e.g., p-toluyl, naphthyl, tert-butyl, dimethylamino, acetylphenyl, hydroxyphenyl, or alkoxy, e.g., methoxy. Such $R_1$ groups when joined with a carbonyl group form an acyl group which preferred for compounds of formula VI include toluoyl, β-naphthoyl, pivaloyl, dimethylcarbamoyl, acetylsalicyloyl, salicyloyl, or alkoxycarbonyl. A preferred secondary amino group may be morpholino.

Examples of 3-acylated analogues of pyridoxal-4,5-aminal include, but are not limited to, 1-morpholino-1,3-dihydro-7-(p-toluoyloxy)-6-methylfuro(3,4-c)pyridine; 1-morpholino-1,3-dihydro-7-(β-naphthoyloxy)-6-methylfuro(3,4-c)pyridine; 1-morpholino-1,3-dihydro-7-pivaloyloxy-6-methylfuro(3,4-c)pyridine; 1-morpholino-1,3-dihydro-7-carbamoyloxy-6-methylfuro(3,4-c)pyridine; and 1-morpholino-1,3-dihydro-7-acetylsalicyloxy-6-methylfuro(3,4-c)pyridine.

Pharmaceutically acceptable acid addition salts of the compounds of formulas V and VI include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., *J. Pharmaceutical Science*, 66: 1–19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The compounds of formula V can be prepared by reacting pyridoxal hydrochloride with an acyl halide in an aprotic solvent. A suitable acyl group is wherein $R_1$ is as defined above. A particularly suitable acyl halide includes p-toluoyl chloride or β-naphthoyl chloride. A suitable aprotic solvent includes acetone, methylethylketone, and the like.

The compounds of formula VI can be prepared by reacting 1-secondary amino-1,3-dihydro-7-hydroxy-6-methylfuro(3,4-c)pyridine with an acyl halide in an aprotic solvent. An acyl group is wherein $R_1$ is as defined above. A particularly suitable acyl halide includes p-toluoyl chloride, β-naphthoyl chloride, trimethylacetyl chloride, dimethylcarbamoyl chloride, and acetylsalicyloyl chloride. A particularly suitable secondary amino group includes morpholino.

The compound 1-morpholino-1,3-dihydro-7-hydroxy-6-methylfuro (3,4-c)pyridine may be prepared by methods known in the art, for example, by reacting morpholine and pyridoxal hydrochloride at a temperature of about 100° C. in a solvent. A suitable solvent includes, for example, toluene. Similarly, other secondary amines as defined for $R_2$ may be used as reactants to prepare the appropriate 1-secondary amino compounds.

The compounds of formula V may alternatively be prepared from the compounds of formula VI by reacting a compound of formula VI with an aqueous acid, such as, for example, aqueous acetic acid.

One skilled in the art would recognize variations in the sequence and would recognize variations in the appropriate reaction conditions from the analogous reactions shown or otherwise known that may be appropriately used in the above-described processes to make the compounds of formula V and VI herein.

The products of the reactions described herein are isolated by conventional means such as extraction, distillation, chromatography, and the like.

In accordance with the present invention, the analogues can be used in the treatment of vitamin $B_6$ deficiency and related diseases; in the treatment of cardiovascular and related diseases; and in the treatment of melanoma and related diseases.

As already discussed, vitamin $B_6$ deficiency and related diseases include, for example, hyperhomocysteinemia and interferences in pathways in which PLP is a coenzyme, for example, glycolysis and aerobic metabolism as well as biosynthesis of neurotransmitters 5-hydroxytryptamine (serotonin) and γaminobutyric acid.

Cardiovascular and related diseases include, for example, hypertension, hypertrophy, congestive heart failure, heart failure subsequent to myocardial infarction, arrhythmia, myocardial ischemia, myocardial infarction, ischemia reperfusion injury, blood coagulation, platelet aggregation, and diseases that arise from thrombotic and prothrombotic states in which the coagulation cascade is activated.

Melanoma and related diseases include, for example, cancer that originates in the pigment-producing cells of the skin and metastasized cancer that originated in the pigment-producing cells of the skin.

"Treatment" and "treating" as used herein include preventing, inhibiting, alleviating, and healing vitamin $B_6$ deficiency and related diseases; cardiovascular and related diseases; melanoma and related diseases; or symptoms thereof. Treatment can be carried out by administering a therapeutically effective amount of a compound of the invention. A "therapeutically effective amount" as used herein includes a prophylactic amount, for example, an amount effective for preventing or protecting against vitamin $B_6$ deficiency and related diseases; cardiovascular and related diseases; melanoma and related diseases; or symptoms thereof, and amounts effective for alleviating or healing vitamin $B_6$ deficiency and related diseases; cardiovascular and related diseases; or melanoma and related diseases; or symptoms thereof.

A physician or veterinarian of ordinary skill readily determines a subject who is exhibiting symptoms of any one or more of the diseases described above. Regardless of the route of administration selected, the compounds of the present invention of formula V or VI or a pharmaceutically acceptable acid addition salt thereof can be formulated into pharmaceutically acceptable unit dosage forms by conventional methods known to the pharmaceutical art. An effective but nontoxic quantity of the compound is employed in treatment. The compounds can be administered in enteral unit dosage forms, such as, for example, tablets, sustained-release tablets, enteric coated tablets, capsules, sustained-release capsules, enteric coated capsules, pills, powders, granules, solutions, and the like. They can also be administered parenterally, such as, for example, subcutaneously, intramuscularly, intradermally, intramammarally, intravenously, and other administrative methods known in the art Although it is possible for a compound of the invention to be administered alone in a unit dosage form, preferably the compound is administered in admixture as a pharmaceutical composition. A pharmaceutical composition comprises a pharmaceutically acceptable carrier and a compound of formula V, VI, or a pharmaceutically acceptable acid addition salt thereof. A pharmaceutically acceptable carrier includes, but is not limited to, physiological saline, ringers, phosphate-buffered saline, and other carriers known in the art. Pharmaceutical compositions can also include additives, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier and therapeutic compound of formula V or VI or a pharmaceutically acceptable acid addition salt thereof are known to those of skill in the art. All methods can include the step of bringing the compound of the invention in association with the carrier and additives. The formulations generally are prepared by uniformly and intimately bringing the compound of the invention into association with a liquid carrier or a finely divided solid carrier or both, and then, if necessary, shaping the product into the desired unit dosage form.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutic amount of a compound of the invention for treating vitamin $B_6$ deficiency and related diseases; cardiovascular and related diseases; melanoma and related diseases; or symptoms thereof, is in a range of about 0.1–100 mg/kg of a patient's body weight, more preferably in the range of about 0.5–50 mg/kg of a patient's body weight, per daily dose. The compound can be administered for periods of short and long duration. Although some individual situations can warrant to the contrary, short-term administration, for example, 30 days or less, of doses larger than 25 mg/kg of a patient's body weight is preferred to long-term administration. When long-term administration, for example, months or years, is required, the suggested dose should not exceed 25 mg/kg of a patient's body weight.

A therapeutically effective amount of a compound for treating the above-identified diseases or symptoms thereof can be administered prior to, concurrently with, or after the onset of the disease or symptom.

The compound can be administered to treat vitamin $B_6$ deficiency and related diseases.

The compound also can be administered to treat cardiovascular and related diseases, for example, hypertrophy, hypertension, congestive heart failure, heart failure subsequent to myocardial infarction, myocardial ischemia, ischemia reperfusion injury, arrhythmia, myocardial infarction, blood coagulation, or platelet aggregation. Preferably, the cardiovascular disease treated is hypertrophy or congestive heart failure. Still preferably, the cardiovascular disease treated is arrhythmia. Also preferably, the cardiovascular disease treated is ischemia reperfusion injury.

The compound can also be administered to treat cardiovascular diseases and other diseases that arise from thrombotic and prothrombotic states in which the coagulation cascade is activated, such as, for example, deep vein thrombosis, disseminated intravascular coagulopathy, Kasabach-Merritt syndrome, pulmonary embolism, myocardial infarction, stroke, thromboembolic complications of surgery, and peripheral arterial occlusion. A compound of the invention may also be useful in the treatment of adult respiratory distress syndrome, septic shock, septicemia, or inflammatory responses, such as edema and acute or chronic atherosclerosis, because thrombin has been shown to activate a large number of cells outside of the coagulation process, such as, for example, neutrophils, fibroblasts, endothelial cells, and smooth muscle cells.

Moreover, the compound can be administered concurrently with compounds that are already known to be suitable for treating the above-identified diseases. For example, methods of the invention include concurrently administering a compound of formula V, VI, or a pharmaceutically acceptable acid addition salt thereof, or a mixture thereof with a therapeutic cardiovascular compound to treat hypertrophy, hypertension, congestive heart failure, heart failure subsequent to myocardial infarction, myocardial ischemia, ischemia reperfusion injury, arrhythmia, or myocardial infarction. Preferably the cardiovascular disease treated is hypertrophy or congestive heart failure. Still preferably, the cardiovascular disease treated is arrhythmia. Also preferably, the cardiovascular disease treated is ischemia reperfusion injury.

Therapeutic cardiovascular compounds that can be concurrently administered with a compound of the invention include an angiotensin converting enzyme inhibitor, an angiotensin II receptor antagonist, a calcium channel blocker, an antithrombolytic agent, a β-adrenergic receptor antagonist, a vasodilator, a diuretic, an α-adrenergic receptor antagonist, an antioxidant, and a mixture thereof. A compound of the invention also can be concurrently administered with PPADS (pyridoxal phosphate-6-azophenyl-2',4'-disulphonic acid), also a therapeutic cardiovascular compound, or with PPADS and another known therapeutic cardiovascular compound as already described.

Preferably a therapeutic cardiovascular compound, which is concurrently administered with a compound of formula V, VI, or a pharmaceutically acceptable acid addition salt thereof, or a mixture thereof, is an angiotensin converting enzyme inhibitor, an angiotensin II receptor antagonist, or a diuretic. Still preferably, the therapeutic cardiovascular compound is an α-adrenergic receptor antagonist. Also preferably, the therapeutic cardiovascular compound is a calcium channel blocker.

These therapeutic cardiovascular compounds are generally used to treat cardiovascular and related diseases as well as symptoms thereof. A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia can be treated by the administration of, for example, angiotensin converting enzyme inhibitor, an angiotensin II receptor antagonist, a calcium channel blocker, an antithrombolytic agent, a β-adrenergic receptor antagonist, a diuretic, an α-adrenergic receptor antagonist, or a mixture thereof. In some instances, congestive heart failure can be treated by the administration of, for example, angiotensin converting enzyme inhibitor, an angiotensin II receptor antagonist, a calcium channel blocker, a vasodilator, a diuretic, or a mixture thereof.

Myocardial infarction can be treated by the administration of, for example, angiotensin converting enzyme inhibitor, a calcium channel blocker, an antithrombolytic agent, a β-adrenergic receptor antagonist, a diuretic, an α-adrenergic receptor antagonist, or a mixture thereof.

Hypertension can be treated by the administration of, for example, angiotensin converting enzyme inhibitor, a calcium channel blocker, a β-adrenergic receptor antagonist, a vasodilator, a diuretic, an α-adrenergic receptor antagonist, or a mixture thereof.

Moreover, arrhythmia can be treated by the administration of, for example, a calcium channel blocker, a β-adrenergic receptor antagonist, or a mixture thereof.

Antithrombolytic agents are used for reducing or removing blood clots from arteries.

Hypertrophy can be treated by the administration of, for example, an angiotensin converting enzyme inhibitor, an angiotensin II receptor antagonist, a calcium channel blocker, or a mixture thereof.

Ischemia reperfusion injury can be treated by the administration of, for example, an angiotensin converting enzyme inhibitor, an angiotensin II receptor antagonist, a calcium channel blocker, or a mixture thereof.

Known angiotensin converting enzyme inhibitors include, for example, captopril, enalapril, lisinopril, benazapril, fosinopril, quinapril, ramipril, spirapril, imidapril, and moexipril.

Examples of known angiotensin II receptor antagonists include both angiotensin I receptor subtype antagonists and angiotensin II receptor subtype antagonists. Suitable antiotensin II receptor antagonists include losartan and valsartan.

Suitable calcium channel blockers include, for example, verapamil, diltiazem, nicardipine, nifedipine, amlodipine, felodipine, nimodipine, and bepridil.

Antithrombolytic agents known in the art include antiplatelet agents, aspirin, and heparin.

Examples of known β-adrenergic receptor antagonists include atenolol, propranolol, timolol, and metoprolol.

Suitable vasodilators include, for example, hydralazine, nitroglycerin, and isosorbide dinitrate.

Suitable diuretics include, for example, furosemide, diuril, amiloride, and hydrodiuril.

Suitable α-adrenergic receptor antagonists include, for example, prazosin, doxazocin, and labetalol.

Suitable antioxidants include vitamin E, vitamin C, and isoflavones.

A compound of formula V or VI, a pharmaceutically acceptable acid addition salt thereof, or a mixture thereof and a therapeutic cardiovascular compound can be administered concurrently. "Concurrent administration" and "concurrently administering" as used herein includes administering a compound of the invention and a therapeutic cardiovascular compound in admixture, such as, for example, in a pharmaceutical composition or in solution, or as separate compounds, such as, for example, separate pharmaceutical compositions or solutions administered consecutively, simultaneously, or at different times but not so distant in time such that the compound of the invention and the therapeutic cardiovascular compound cannot interact and a lower dosage amount of the active ingredient cannot be administered.

A compound of formula V or VI, a pharmaceutically acceptable acid addition salt thereof, or a mixture thereof also can be administered to treat melanoma and related diseases.

The method of the invention also includes concurrently administering a compound of formula V or VI, a pharmaceutically acceptable acid addition salt thereof, or a mixture thereof with interleukin-2 immunotherapy to treat melanoma and related diseases.

"Concurrent administration" and "concurrently administering" as used herein includes administering a compound of formula V or VI, a pharmaceutically acceptable acid addition salt thereof, or a mixture thereof and interleukin-2 immunotherapy in admixture, such as, for example, in a pharmaceutical composition, or as separate compounds, such as, for example, separate pharmaceutical compositions administered consecutively, simultaneously, or at different times. Preferably, if the compound and interleukin-2 immunotherapy are administered separately, they are not administered so distant in time from each other that the compound and the interleukin-2 immunotherapy cannot interact and a lower dosage amount of interleukin-2 immunotherapy cannot be administered.

This invention will be further characterized by the following examples. These examples are not meant to limit the scope of the invention, which has been fully set forth in the foregoing description. Variations within the scope of the invention will be apparent to those skilled in the art.

EXAMPLES

All reagents used in the following Examples can be purchased from Aldrich (Milwaukee, Wis. or Allentown, Pa.).

Example 1

Synthesis of morpholine pyridoxal-4.5-aminal (1-morpholino-1,3-dihydro-7-hydroxy-6-methylfuro(3.4-c) pyridine)

A mixture of morpholine (20 g) and toluene (100 mL) was stirred and heated using an oil bath set to 100° C. for 15 minutes. Pyridoxal hydrochloride (10 g) was then added and the reaction mixture was stirred at 100° C. for two hours. The reaction mixture was then concentrated by distillation of the toluene and morpholine. The concentrated reaction mixture was washed three times by adding toluene (100 mL) and removing the toluene by distillation. After washing, the residue was dissolved in toluene and filtered, and then hexane was added until precipitation began, at which time the reaction mixture was left overnight at room temperature. Crystals were collected and washed thoroughly with hexane.

Nuclear magnetic resonance spectroscopy (NMR) and mass spectroscopy confirmed the identity of the synthesized compound. The purity of the compound was analyzed by high performance liquid chromatography (HPLC) using a C-18 reverse phase column and water/acetonitrile as solvent (1–100% acetonitrile over 25 minutes).

The product can be represented by the formula:

Example 2

Synthesis of the 3-toluate of the morpholine pyridoxal-4,5-aminal (1-morpholino-1,3-dihydro-7-(p-toluoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The reaction mixture was cooled to between 0 and 5° C. and then p-toluoyl chloride (1.06 g, 6 mmoles) in acetone (20 mL) was added. This mixture was stirred for two hours, followed by filtering out the solid and evaporating the solution to dryness under vacuum. The residue was chromatographed on silica gel using a mixture of ethyl acetate and hexane as solvent.

The purified solid was analyzed by thin layer chromatography (TLC), NMR, and mass spectroscopy. The purity of the synthesized compound was confirmed by HPLC as described in Example 1.

The product can be represented by the formula:

Example 3
Synthesis of the 3-toluate of pyridoxal (2-methyl-3-toluoyloxy-4-formyl-5-hydroxymethylpyridine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then p-toluoyl chloride (2.12 g, 12 mmoles) in acetone (20 mL) was added. The reaction mixture was stirred for two hours followed by filtering out the solid and evaporating the solution to dryness under vacuum. The residue was chromatographed on silica gel as described in Example 2.

The purified solid was analyzed by TLC, NMR, and mass spectroscopy. The purity of the compound was confirmed by HPLC as described in Example 1.

Alternative to the above-described method, the 3-toluate of pyridoxal is synthesized by reacting the compound of Example 2 with 80% aqueous acetic acid at 60° C. for 30 minutes, and then diluting with water and extracting by ethyl acetate. The ethyl acetate layer is washed with 5% aqueous sodium bicarbonate, dried with magnesium sulfate, and evaporated to dryness. The compound is also analyzed as described supra.

The product can be represented by the formula:

Example 4
Synthesis of 3-β-naphthoate of the morpholine pyridoxal-4,5-aminal (1-morpholino-1,3-dihydro-7-(β-naphthoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.1 g, 5 mmoles) were mixed in a nitrogen-cooled, dry flask. The mixture was cooled to between 0 and 5° C. and then β-naphthoyl chloride (1.06 g, 6 mmoles) in acetone (20 mL) was added. The reaction mixture was stirred for two hours, and then the solid was filtered out and the solution was evaporated to dryness under vacuum. The residue was chromatographed according to Example 2.

The purified solid was analyzed according to Example 2, and the purity was confirmed according to Example 1.

The product can be represented by the formula:

Example 5
Synthesis of the 3-β-naphthoate of pyridoxal (2-methyl-3-β-naphthoyloxy-4-formyl-5-hydroxymethylpyridine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then β-naphthoyl chloride (2.12 g, 12 mmoles) in acetone (20 mL) was added and the mixture was stirred for two hours. The solid was filtered out and the solution was evaporated to dryness under vacuum. The residue was chromatographed according to Example 2.

The purified solid was analyzed according to Example 2, and the purity was confirmed according to Example 1.

Alternative to the above-described synthesis, the 3β-naphthoate of pyridoxal is prepared by reacting the compound of Example 4 with 80% aqueous acetic acid at 60° C. for 30 minutes, followed by diluting with water and extracting by ethyl acetate. The ethyl acetate layer is then washed with 5% aqueous sodium bicarbonate, dried with magnesium sulfate, and evaporated to dryness. The compound is also analyzed as described supra.

The product can be represented by the formula:

Example 6
Synthesis of 3-pivaloyl of the morpholine pyridoxal-4,5-aminal (1-morpholino-1,3-dihydro-7-pivaloyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then pivaloyl chloride (trimethylacetyl chloride) (720 mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

The product can be represented by the formula:

Example 7
Sypnthesis of 3-dimethylcarbamoyl of the morpholine pyridoxal-4,5-aminal (1-morpholino-1,3-dihydro-7-(dimethylcarbamoyloxy)-6-methylfiiro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then dimethylcarbamoyl chloride (642 mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

The product can be represented by the formula:

Example 8
Synthesis of 3-acetylsalicyloyl of the morpholine pyridoxal-4,5-aminal (1-morpholino-1,3-dihydro-7-acetylsalicyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then acetylsalicyloyl chloride (1.09 g, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

The product can be represented by the formula:

Example 9
Bioavailability of Pyridoxal-5'-Phosphate and Pyridoxal after the Administration of a Compound of the Invention The bioavailability of pyridoxal-5'-phosphate and pyridoxal after the administration of a compound of the invention was determined by measuring pyridoxal-5'-phosphate and pyridoxal levels in blood plasma after administering a compound of the invention to rats.

The rats studied were twelve male Sprague-Dawley rats (Charles River, Montreal, Canada) chosen at random. These rats were divided into four groups. The first group was administered pyridoxal-5'-phosphate (Sigma, Milwaukee, Wis.) as a control; the second group was administered 3-pivaloylaminal (synthesized according to Example 6); the third group was administered 3-dimethylcarbamoylaminal (synthesized according to Example 7); and the fourth group was administered 3-acetylsalicoylaminal (synthesized according to Example 8).

Approximately 24 to 48 hours prior to administering pyridoxal-5'-phosphate or a compound of the invention to the rats, an initial blood sample (500–600 µL) was obtained from each rat. The blood samples were collected from the orbital sinus of each rat according to standard methods. The blood samples were placed into EDTA-Microtainer Brand Tubes (Becton Dickinson) and the plasma was separated from blood by centrifugation. The plasma samples were stored at −80° C. After withdrawal of the blood sample, each rat was then intravenously injected with saline in an amount equivalent to the blood withdrawn.

Each rat fasted for eight hours prior to administering pyridoxal-5'-phosphate or a compound of the invention. Each rat then received by oral gavage pyridoxal-5'-phosphate or a compound of the invention (10 mg/kg of body weight) according to the group with which the rat was identified.

Blood samples were then collected from each rat as described above and stored as described above. Blood samples were collected at about 15, 30, 60, 180, 360, 720, 1440, and 2160 minutes after administration of pyridoxal-5'-phosphate or the compound of the invention.

After all samples were collected, the frozen plasma samples were thawed at about room temperature, and the pyridoxal-5'-phosphate and pyridoxal levels were determined for each sample. To determine the pyridoxal-5'-phosphate and pyridoxal levels, the protein was first precipitated from the plasma. Each sample of protein-free plasma was then combined with perchloric acid and phosphate buffer. Each sample was then evaluated by high performance liquid chromatography on a C-18 reverse-phase silica-gel column. Each sample was detected with excitation at 300 mm and emission at 400 mm. The amounts of pyridoxal-5'-phosphate and pyridoxal were quantified using standard curve and integration of the peaks. The results are shown in FIGS. 1–4.

Figure 1:
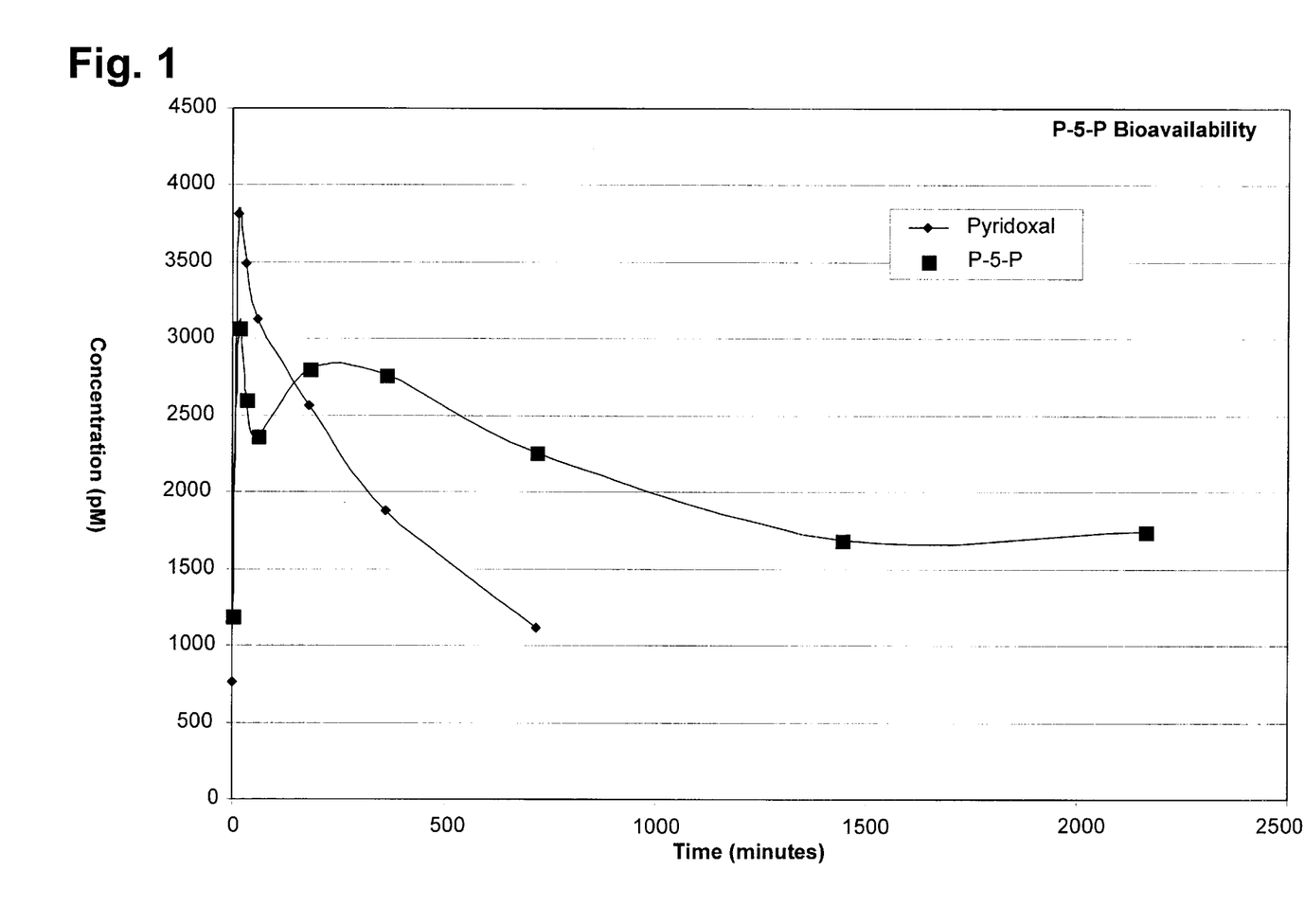
FIG. 1 shows pyridoxal and pyridoxal-5'-phosphate plasma levels in rats after administration of pyridoxal-5'-phosphate.
Figure 2:
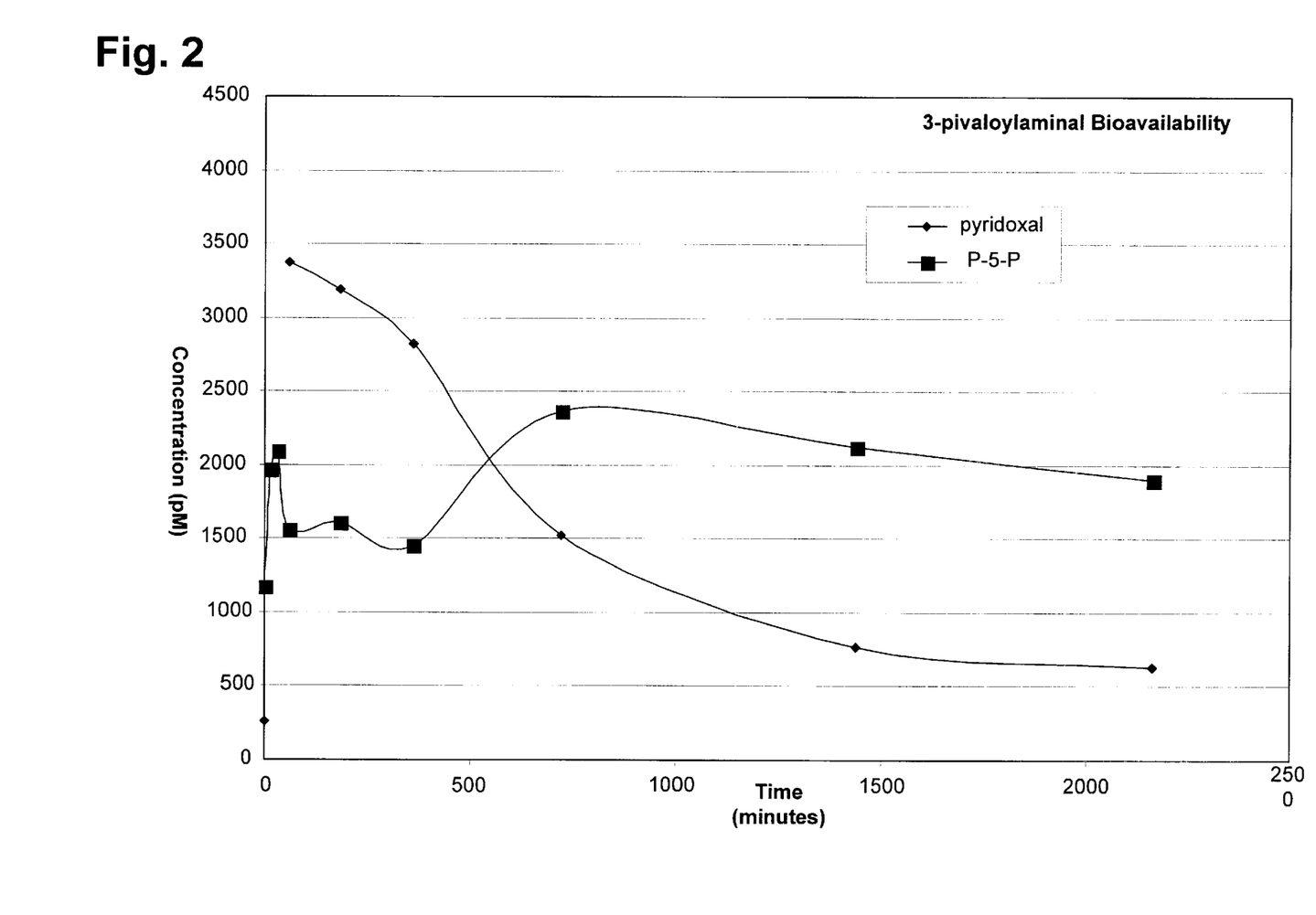
FIG. 2 shows pyridoxal and pyridoxal-5'-phosphate plasma levels in rats after administration of 3-pivaloylaminal.
Figure 3:
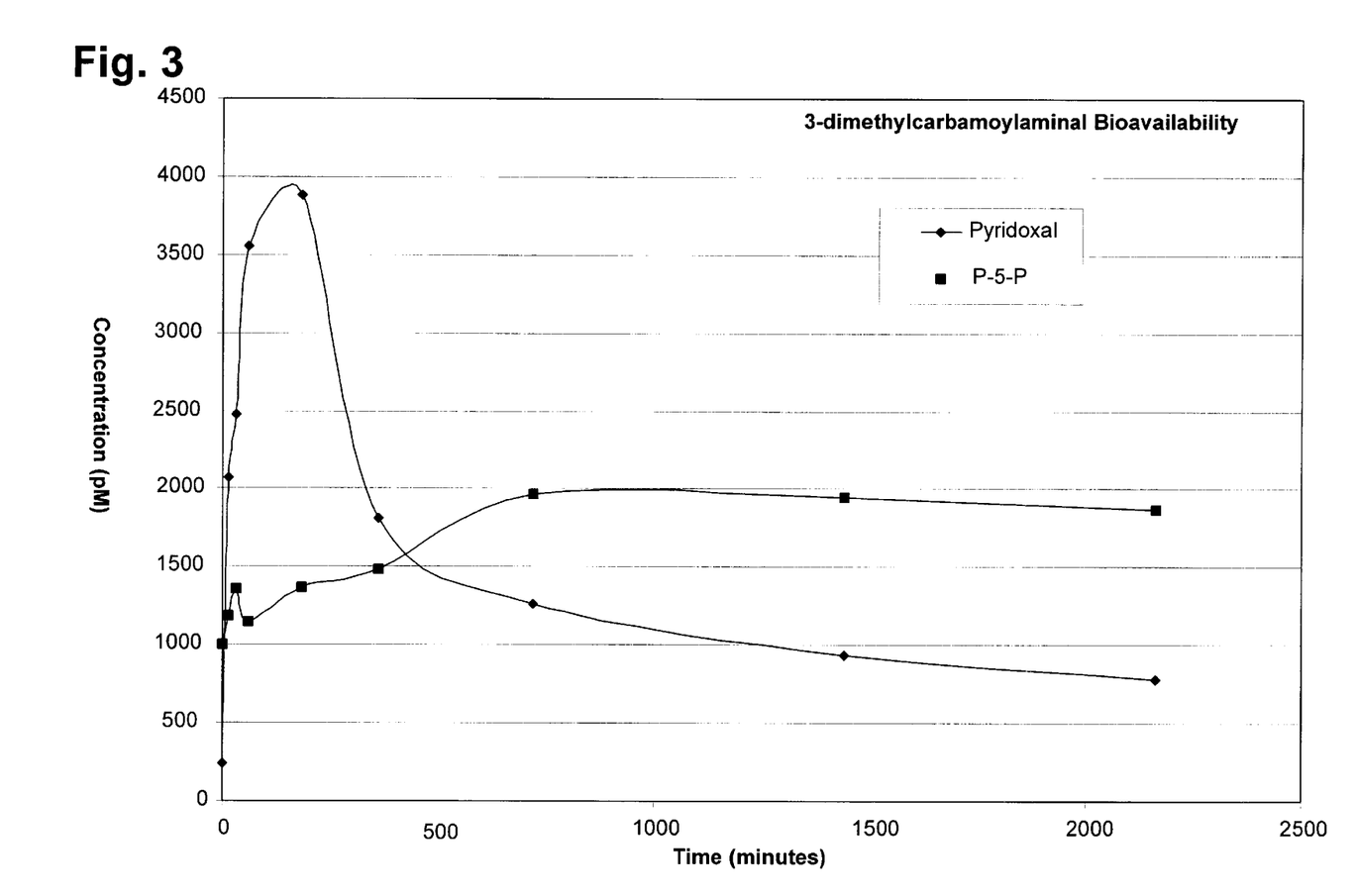
FIG. 3 shows pyridoxal and pyridoxal-5'-phosphate plasma levels in rats after administration of 3-dimethylcarbamoylaminal.
Figure 4:
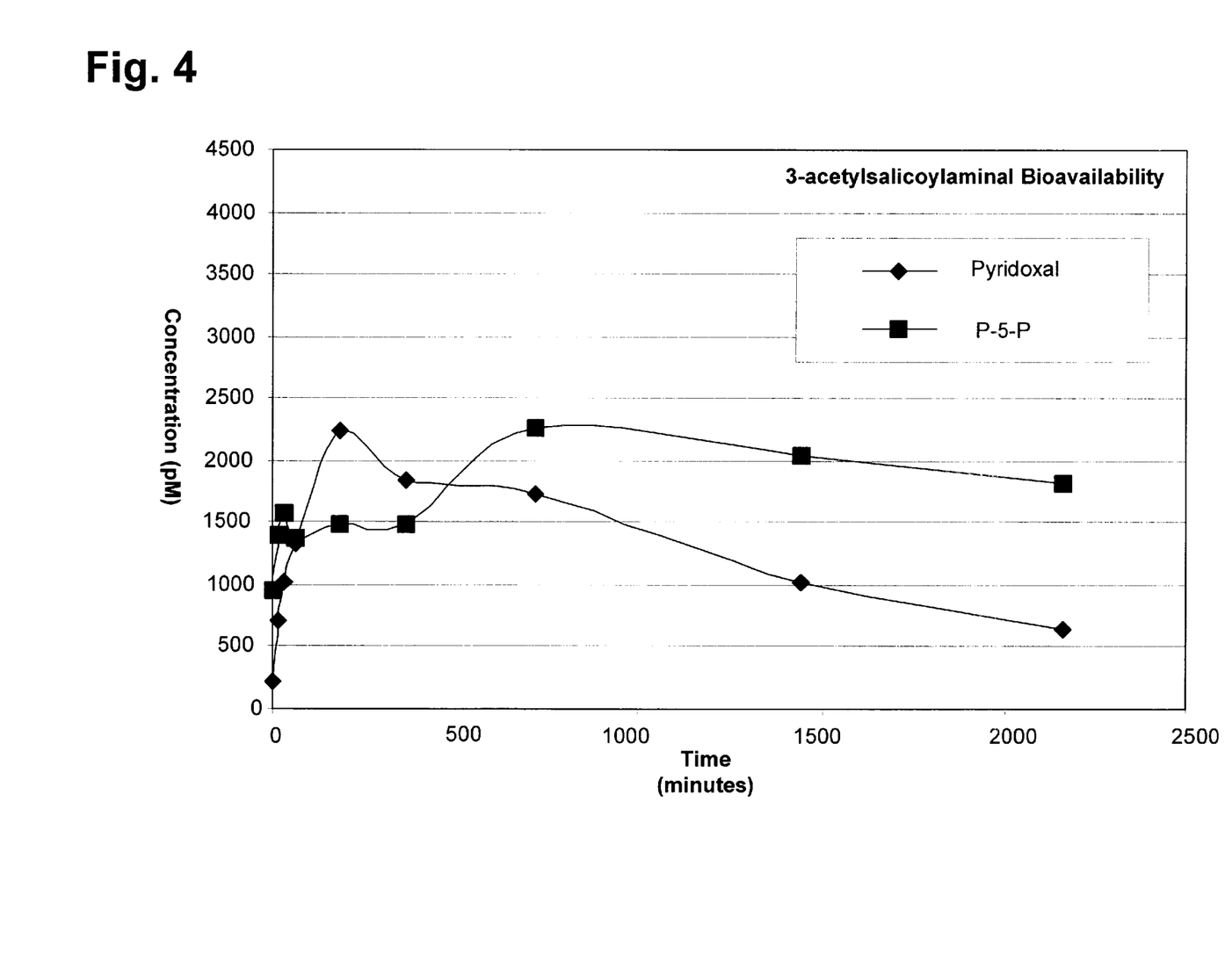
FIG. 4 shows pyridoxal and pyridoxal-5'-phosphate plasma levels in rats after administration of 3-acetylsalicoylaminal.

The results show that 3-pivaloylaminal (FIG. 2), 3-dimethylcarbamoylaminal (FIG. 3), and 3-acetylsalicoylaminal (FIG. 4) provided pyridoxal and pyridoxal-5'-phosphate levels comparable to the levels provided by administering pyridoxal-5'-phosphate (FIG. 1).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

Although embodiments of the invention have been described above, it is not limited thereto, and it will be apparent to persons skilled in the art that numerous modifications and variations form part of the present invention insofar as they do not depart from the spirit, nature, and scope of the claimed and described invention.

What is claimed is:

1. A compound of the formula or a pharmaceutically acceptable acid addition salt thereof; wherein $R_1$ is alkyl,
    alkenyl,
        in which alkyl or alkenyl can be interrupted by nitrogen, oxygen, or sulfur, and can be substituted at the terminal carbon by hydroxy, alkoxy, alkanoyloxy, alkanoyloxyaryl, alkoxyalkanoyl, alkoxycarbonyl, or dialkylcarbamoyloxy;
    alkoxy;
    dialkylamino;
    alkanoyloxy;
    alkanoyloxyaryl;
    alkoxyalkanoyl;
    alkoxycarbonyl;
    dialkylcarbamoyloxy; or
    aryl,
    aryloxy,
    arylthio, or
    aralkyl,
        in which aryl can be substituted by alkyl, alkoxy, amino, hydroxy, halo, nitro, or alkanoyloxy; and $R_2$ is a secondary amino group.

2. A compound according to claim 1, wherein $R_1$ is phenyl or naphthyl in which phenyl or naphthyl is unsubstituted or substituted by one or more groups of $C_{1-4}$ alkyl, $C_{1-4}$ alkoxy, amino, hydroxy, halo, nitro, or $C_{1-4}$ alkanoyloxy.

3. A compound according to claim 1, wherein $R_1$ is (2-acetoxy-2-methyl)propanyl, dimethylamino, or 1-ethanoyloxy-1-methylethyl.

4. A compound according to claim 1, wherein $R_1$ is tert-butyl.

5. A compound according to claim 1, wherein $R_1$ is methoxy or ethoxy.

6. A compound according to claim 1, wherein $R_1$ is toluyl, naphthyl, phenyl, or 1-ethanoyloxyphenyl.

7. A compound according to claim 1, wherein $R_1$ is dimethylamino, acetylsalicyl, or 2,2-dimethylethyl.

8. A compound according to claim 1, wherein $R_2$ is a group of the formula wherein $R_3$ and $R_4$ are each independently alkyl or when taken together form a ring with the nitrogen atom and which ring may optionally be interrupted by a nitrogen or oxygen atom.

9. A compound according to claim 8, wherein $R_2$ is piperidino.

10. A compound according to claim 8, wherein $R_2$ is morpholino or piperazino.

11. The compound of claim 1 that is 1-morpholino-1,3-dihydro-7-(β-toluoyloxy)-6-methylfuro(3,4-c)pyridine.

12. The compound of claim 1 that is 1-morpholino-1,3-dihydro-7-(β-naphthoyloxy)-6-methylfuro(3,4-c)pyridine.

13. The compound of claim 1 that is 1-morpholino-1,3-dihydro-7-pivaloyloxy-6-methylfuro(3,4-c)pyridine.

14. The compound of claim 1 that is 1-morpholino-1,3-dihydro-7-(dimethylcarbamoyloxy-6-methylfuro(3,4-c)pyridine.

15. The compound of claim 1 that is 1-morpholino-1,3-dihydro-7-acetylsalicyloxy-6-methylfuro(3,4-c)pyridine.

16. A pharmaceutical composition comprising: a pharmaceutically acceptable carrier and a therapeutically effective amount of a compound according to claim 1.

17. A pharmaceutical composition of claim 16, wherein the pharmaceutical composition is in a form suitable for enteral or parenteral administration.

18. A pharmaceutical composition of claim 16, wherein the compound is selected from the group consisting of 1-morpholino-1,3-dihydro-7-(p-toluoyloxy)-6-methylfuro(3,4-c)pyridine, 1-morpholino-1,3-dihydro-7-(β-naphthoyloxy)-6-methylfuro(3,4-c)pyridine, 1-morpholino-1,3-dihydro-7-pivaloyloxy-6-methylfuro(3,4-c)pyridine, 1-morpholino-1,3-dihydro-7-carbamoyloxy-6-methylfuro(3,4-c)pyridine, 1-morpholino-1,3-dihydro-7-acetylsalicyloxy-6-methylfuro(3,4-c)pyridine, and a pharmaceutically acceptable acid addition salt thereof.

19. A method of treating vitamin $B_6$ deficiency in a mammal comprising: administering to the mammal a therapeutically effective amount of a compound according to claim 1 in a unit dosage form.

20. The method of claim 19, wherein the compound is administered enterally or parenterally.

21. A method of treating hyperhomocysteinemia in a mammal comprising: administering to the mammal a therapeutically effective amount of a compound according to claim 1 in a unit dosage form.

22. The method of claim 21, wherein the compound is administered enterally or parenterally.

23. A method of treating interferences in glycolysis, aerobic metabolism, biosynthesis of serotonin, or biosynthesis of γ-aminobutyric acid in a mammal comprising: administering to the mammal a therapeutically effective amount of a compound according to claim 1 in a unit dosage form.

24. The method of claim 23, wherein the compound is administered enterally or parenterally.

25. A method of treating hypertension in a mammal comprising: administering to the mammal a therapeutically effective amount of a compound according to claim 1 in a unit dosage form.

26. The method of claim 25, wherein the compound is administered enterally or parenterally.

27. The method of claim 25, wherein the compound is administered concurrently with a therapeutic cardiovascular compound selected from the group consisting of an angiotensin converting enzyme inhibitor, a calcium channel blocker, a β-adrenergic receptor antagonist, a vasodilator, a diuretic, an α-adrenergic receptor antagonist, and a mixture thereof.

28. A method of treating myocardial infarction in a mammal comprising: administering to the mammal a therapeutically effective amount of a compound according to claim 1, in a unit dosage form.

29. The method of claim 28, wherein the compound is administered enterally or parenterally.

30. The method of claim 28, wherein the compound is administered concurrently with a therapeutic cardiovascular compound selected from the group consisting of an angiotensin converting enzyme inhibitor, a calcium channel blocker, an antithromblytic agent, a β-adrenergic receptor antagonist, a diuretic, an α-adrenergic receptor antagonist, and a mixture thereof.

31. A method of treating ischemia reperfusion injury in a mammal comprising: administering to the mammal a therapeutically effective amount of a compound according to claim 1 in a unit dosage form.

32. The method of claim 31, wherein the compound is administered enterally or parenterally.

33. The method of claim 31, wherein the compound is administered concurrently with a therapeutic cardiovascular compound selected from the group consisting of an angiotensin converting enzyme inhibitor, an angiotensin II receptor antagonist, a calcium channel blocker, and a mixture thereof.

34. A method of treating myocardial ischemia in a mammal comprising: administering to the mammal a therapeutically effective amount of a compound according to claim 1 in a unit dosage form.

35. The method of claim 34, wherein the compound is administered enterally or parenterally.

36. The method of claim 36, wherein the compound is administered concurrently with a therapeutic cardiovascular compound selected from the group consisting of an angiotensin converting enzyme inhibitor, an angiotensin II receptor antagonist, a calcium channel blocker, an antithrombolytic agent, a β-adrenergic receptor antagonist, a diuretic, an α-adrenergic receptor antagonist, and a mixture thereof.

37. A method of treating congestive heart failure in a mammal comprising: administering to the mammal a therapeutically effective amount of a compound according to claim 1 in a unit dosage form.

38. The method of claim 37, wherein the compound is administered enterally or parenterally.

39. The method of claim 37, wherein the compound is administered concurrently with a therapeutic cardiovascular compound selected from the group consisting of an angiotensin converting enzyme inhibitor, an angiotensin II receptor antagonist, a calcium channel blocker, a vasodilator, a diuretic, and a mixture thereof.

40. A method of treating arrhythmia in a mammal comprising: administering to the mammal a therapeutically effective amount of a compound according to claim 1 in a unit dosage form.

41. The method of claim 40, wherein the compound is administered enterally or parenterally.

42. The method of claim 40, wherein the compound is administered concurrently with a therapeutic cardiovascular compound selected from the group consisting of a calcium channel blocker, a β-adrenergic receptor antagonist, and a mixture thereof.

43. A method of treating blood coagulation in a mammal comprising: administering to the mammal a therapeutically effective amount of a compound according to claim 1, in a unit dosage form.

44. The method of claim 43, wherein the compound is administered enterally or parenterally.

45. The method of claim 43, wherein the compound is administered concurrently with an antithrombolytic agent.

46. A method of treating hypertrophy in a mammal comprising: administering to the mammal a therapeutically effective amount of a compound according to claim 1 in a unit dosage form.

47. The method of claim 46, wherein the compound is administered enterally or parenterally.

48. The method of claim 46, wherein the compound is administered concurrently with a therapeutic cardiovascular compound selected from the group consisting of an angiotensin converting enzyme inhibitor, an angiotensin II receptor antagonist, a calcium channel blocker, and a mixture thereof.

49. A method of treating a disease that arises from thrombotic and prothrombotic states in which the coagulation cascade is activated in a mammal comprising: administering to the mammal a therapeutically effective amount of a compound according to claim 1 in a unit dosage form.

50. The method of claim 49, wherein the compound is administered enterally or parenterally.

51. The method of claim 49, wherein the disease comprises deep vein thrombosis.

52. The method of claim 49, wherein the disease comprises disseminated intravascular coagulopathy.

53. The method of claim 49, wherein the disease comprises pulmonary embolism.

54. A method of treating platelet aggregation in a mammal comprising: administering to the mammal a therapeutically effective amount of a compound according to claim 1 in a unit dosage form.

55. The method according to claim 54 wherein the compound is administered enterally or parenterally.

56. A method of treating melanoma in a mammal comprising: administering to the mammal a therapeutically effective amount of a compound according to claim 1 in a unit dosage form.

57. The method of claim 56, wherein the compound is administered enterally or parenterally.

* * * * *

UNITED STATES PATENT AND TRADEMARK OFFICE
CERTIFICATE OF CORRECTION

PATENT NO.    : 6,339,085 B1
DATED         : January 15, 2002
INVENTOR(S)   : Haque et al.

It is certified that error appears in the above-identified patent and that said Letters Patent is hereby corrected as shown below:

<u>Title page,</u>
Item [54], insert -- NOVEL -- as first word in title.
Item [75], Inventor, insert -- James L. Charlton, Winnipeg, Manitoba (CA) -- as the second-named inventor.
Item [73], "Medicore" should read -- Medicure --; and "Winnepeg" should read
-- Winnipeg --
Item [56], References Cited, FOREIGN PATENT DOCUMENTS, insert the following references.
--      FR      5.801 M         03/1968
        FR      2 034 539       12/1970
        WO      WO 99/53928     10/1999 --
OTHER PUBLICATIONS, insert the following references:

--Aybak, M. et al., "Effect of Oral Pyridoxine Hydrochloride Supplementation on Arterial Blood Pressure in Patients with Essential Hypertension", *Drug Res.*, Vol. 45, No. 12, pp. 1271-1273 (1995).

Bhagavan, H. et al., "Effect of Postweanling Pyridoxine Deficiency on Growth and Concentration of the Coenzyme Pyridoxal-5'-phosphate in Heart, Kidneys, Lungs, and Adrenals in Rats", *Pediat. Res.*, Vol. 10, pp. 730-732 (1976).

Folsom, A. et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study",
Circulation, Vol. 98, pp. 204-210 (July 21, 1998).

Kubyshkin, V. et al., "Comparative characteristics of the arrhythmic syndrome and the possibility for its coenzyme correction in dilated and hypertrophic cardiomyopathy", *Abstract*, 1 pg. (1989).

Levy, H. et al., "Pyridoxine Deficiency in Congestive Heart Failure", *P.S.E.B.M.*, Vol. 101, pp. 617-621 (1959)

Mendelsohn, A. et al., "Hemodynamic and Clinical Effects of Oral Levodopa in Children With Congestive Heart Failure", *JACC*, Vol. 30, No. 1, pp. 237-242 (July 1997).

Mulvaney, D. et al., "Electrocardiographic changes in vitamin $B_6$ deficient rats", *Cardiovascular Research*, Vol. 13, pp. 506-513 (1979).

Takuma, Y. et al., "Combination Therapy of Infantile Spasms With High-Dose Pyridoxal Phosphate and Low-Dose Corticotropin", *Journal of Child Neurology*, Vol. 11, No. 1, pp. 35-40 (January 1996).

Vidrio, H., "Interaction with Pyridoxal as a Possible Mechanism of Hydralazine Hypotension", *Journal of Cardiovascular Pharmacology*, Vol. 15, pp. 150-156 (1990).--

UNITED STATES PATENT AND TRADEMARK OFFICE
CERTIFICATE OF CORRECTION

PATENT NO.    : 6,339,085 B1
DATED         : January 15, 2002
INVENTOR(S)   : Haque et al.

It is certified that error appears in the above-identified patent and that said Letters Patent is hereby corrected as shown below:

Column 22,
Line 20, "(ß-toluoyloxy)" should read -- (*p*-toluoyloxy) --

Column 23,
Line 43, "claim 36" should read -- claim 34 --

Signed and Sealed this

Eighth Day of July, 2003

JAMES E. ROGAN
*Director of the United States Patent and Trademark Office*